United States Patent
Rhoades et al.

(10) Patent No.: US 7,842,678 B2
(45) Date of Patent: Nov. 30, 2010

(54) COMPOSITIONS COMPRISING OLIGOSACCHARIDES

(75) Inventors: Jonathan R Rhoades, Reading (GB); Robert Rastall, Reading (GB); Glenn R. Gibson, Reading (GB)

(73) Assignee: Nestec S.A., Vevey (CH)

( * ) Notice: Subject to any disclaimer, the term of this patent is extended or adjusted under 35 U.S.C. 154(b) by 746 days.

(21) Appl. No.: 10/572,664

(22) PCT Filed: Sep. 17, 2004

(86) PCT No.: PCT/EP2004/010469

§ 371 (c)(1), (2), (4) Date: Mar. 20, 2006

(87) PCT Pub. No.: WO2005/027663

PCT Pub. Date: Mar. 31, 2005

(65) Prior Publication Data

US 2006/0287276 A1 Dec. 21, 2006

(30) Foreign Application Priority Data

Sep. 19, 2003 (GB) .................................. 0321996.1

(51) Int. Cl.
*A61K 31/715* (2006.01)
*C07H 3/06* (2006.01)

(52) U.S. Cl. .................... 514/54; 514/61; 536/123.1

(58) Field of Classification Search ...................... None
See application file for complete search history.

(56) References Cited

U.S. PATENT DOCUMENTS

| | | | |
|---|---|---|---|
| 4,895,838 A * | 1/1990 | McCluer et al. | 514/54 |
| 5,260,280 A * | 11/1993 | Isoda et al. | 514/25 |
| 5,322,836 A * | 6/1994 | Tomita et al. | 514/6 |
| 5,459,257 A * | 10/1995 | Shoji et al. | 536/118 |
| 5,683,991 A | 11/1997 | Jurenitsch et al. | |
| 5,906,982 A * | 5/1999 | Prieto et al. | 514/61 |
| 6,399,124 B1 * | 6/2002 | Lesens et al. | 426/61 |
| 6,429,202 B1 * | 8/2002 | Bombardelli et al. | 514/78 |
| 6,613,549 B2 * | 9/2003 | Reid et al. | 424/93.45 |
| 6,750,331 B1 * | 6/2004 | Takaichi et al. | 536/1.11 |
| 6,863,918 B2 * | 3/2005 | Bindels et al. | 426/590 |
| 7,053,067 B2 * | 5/2006 | Kuo et al. | 514/54 |

FOREIGN PATENT DOCUMENTS

| | | | |
|---|---|---|---|
| EP | 1010372 A2 * | | 6/2000 |
| WO | WO 98/42311 | | 10/1998 |
| WO | WO00/49885 | * | 8/2000 |
| WO | WO01/17365 | * | 3/2001 |
| WO | WO 01/65949 | | 9/2001 |
| WO | WO 02/051264 | | 7/2002 |
| WO | WO03/026677 | * | 4/2003 |
| WO | WO2004/002495 | * | 8/2004 |

OTHER PUBLICATIONS

Martin-Sosa et al., "The Sialylated Fraction of Milk Oligosaccharides Is Partially Responsible for Binding to Enterotoxigenic and Uropathogenic *Escherichia coli* Human Strains" Journal of Nutrition (2002) vol. 132, pp. 3067-3072.*
Yokoyama et al., "Synthesis of 0I+6-Mannooligosaccharides in *Mycobacterium smegmatis*" The Journal of Biological Chemistry (1989) vol. 264, No. 36, pp. 21621-21628.*
Merriam-Webster's Collegiate Dictionary, Tenth Edition, published 1998 by Merriam-Webster, Incorporated, pp. 924 and 935.*
Tuohy et al. "The prebiotic effects of biscuits containing partially hydrolysed guar gum and fructo-oligosaccharides—a human volunteer study" British Journal of Nutrition (2001) vol. 86, pp. 341-348.*
Lee et al., "Chitosan oligosaccharides, dp 2-8, have prebiotic effect on the *Bifidobacterium bifidium* and *Lactobacillus* sp." Anaerobe (2002) vol. 8 pp. 319-324.*
Patrick et al., "Effect of Supplements of partially hydrolyzed guar gum on the occurrence of constipation and use of laxative agents" Journal of the American Dietetic Association (1998) vol. 98 No. 8, pp. 912-914.*
Takahashi et al., "Effect of Partially Hydrolyzed Guar Gum on Fecal Output in Human Volunteers" Nutrition Research (1993) vol. 13 pp. 649-657.*
The Merck Manual of Diagnosis and Terapy, published 1999 by Merck Research Laboratories, pp. 1655-1658.*
Weisman et al., "Biosynthesis of Mycobacterial Methylmannose Polysaccharide" The Journal of Biological Chemistry (1984) vol. 259 No. 6, pp. 3464-3469.*
Zimmermann, et al, "Pro-And Prebiotics in Pig Nutrition-Potential Modulators of Gut Health", Journal of Animal and Feed Sciences, vol. 10, No. 1, pp. 47-56, (2001).
Macfarlane et al, "Probiotics and Prebiotics: Can Regulating the Activities of Intestinal Bacteria Benefit Health?", British Medical Journal, vol. 318, No. 7189, pp. 999-1003, (1999).

* cited by examiner

*Primary Examiner*—Eric S Olson
(74) *Attorney, Agent, or Firm*—Gary M. Lobel

(57) ABSTRACT

The present invention concerns compositions comprising a saccharide for the inhibition of pathogen adhesion to mammalian cells.

12 Claims, 6 Drawing Sheets

COMPOSITIONS COMPRISING OLIGOSACCHARIDES

The present invention concerns the use of saccharides, e.g. oligosaccharides, as inhibitors of pathogen adhesion to mammalian cells, especially of mammalian gut cells, nutritional compositions comprising a saccharide, e.g. oligosaccharide, for the inhibition of pathogen adhesion to mammalian cells and a method for the screening of a saccharide, e.g. oligosaccharide, useful as inhibitor of pathogen adhesion to mammalian cells.

For many gut bacteria, the first stage in pathogenicity is adherence to the gut wall. For this to take place, the bacteria initially attach to particular receptor molecules on the epithelial cell surface, which is mediated by specific carbohydrate groups on the epithelial cell. According to the present invention it has been surprisingly found that saccharides, e.g. oligosaccharides, which mimic these groups can competitively inhibit bacterial binding and reduce the incidence and severity of disease.

In particular, present inventors have identified compounds which survive passage through the gastrointestinal tract and inhibit the adhesion of specific pathogens to the colonic epithelium without adversely affecting the colonic microflora or adhesion of probiotic organisms.

In one aspect of the present invention it has now surprisingly been found that compounds chosen from at least one of manno-oligosaccharide, e.g. alpha 1-2 manno-oligosaccharide, alpha 1-3 manno-oligosaccharide, alpha 1-6 manno-oligosaccharide, e.g. alpha 1-2 mannobiose, alpha 1-3 mannobiose, alpha 1-6 mannobiose; methyl manno-oligosaccharide, e.g. methyl alpha manno-oligosaccharide; caseinoglycomacropeptide (CGMP); chito-oligosaccharide; fructo-oligosaccharide (FOS); pectic oligosaccharide; galacto-oligosaccharide (GOS); curdlan (beta-1,3-glucan); sialyl-oligosaccharide; lactose; lactulose; lactosucrose; isomalto-oligosaccharide; oligogalacturonide; partially hydrolysed guar gum; xylo-oligosaccharide; gentio-oligosaccharide; arabino-oligosaccharide, pectin and long-chain isomalto-oligosaccharide, hereinafter referred to as "compounds of the invention", show strong antiadhesive activity.

In one embodiment of the invention, the preferred compounds of the invention may comprise manno-oligosaccharide, e.g. alpha 1-2 mannobiose, alpha 1-3 mannobiose, alpha 16 mannobiose; methyl manno-oligosaccharide, e.g. methyl alpha manno-oligosaccharide, CGMP; chito-oligosaccharide; pectic oligosaccharide; curdlan; sialyl-oligosaccharide; lactose; lactulose; lactosucrose; isomalto-oligosaccharide; oligogalacturonide; partially hydrolysed guar gum; xylo-oligosaccharide; gentio-oligosaccharide; arabino-oligosaccharide; long-chain isomalto-oligosaccharide; pectin or mixture thereof.

In another embodiment of the invention, the compounds of the invention may comprise manno-oligosaccharide, e.g. alpha 1-2 mannobiose, alpha 1-3 mannobiose, alpha 1-6 mannobiose; methyl manno-oligosaccharide, e.g. methyl alpha manno-oligosaccharide; pectic oligosaccharide; sialyl oligosaccharide; chito oligosaccharide; CGMP; GOS; partially hydrolysed guar gum; xylo-oligosaccharide; lactulose; or mixture thereof.

In yet another embodiment of the invention, the compounds of the invention may comprise manno-oligosaccharide, e.g. alpha 1-2 mannobiose, alpha 1-3 mannobiose, alpha 1-6 mannobiose; methyl manno-oligosaccharide, e.g. methyl alpha manno-oligosaccharide; pectic oligosaccharide; sialyl oligosaccharide; chito oligosaccharide; CGMP; or mixture thereof.

In a further aspect the present invention pertains to the use of a composition comprising a compound of the invention for the manufacture of a nutritional or pharmaceutical composition for the inhibition of pathogen adhesion to mammalian cells, e.g. gut mammalian cells, and/or for reducing or inhibiting the invasion and infection of mammalian cells, e.g. gut mammalian cells, by pathogen.

In one embodiment of the invention, the composition of the invention may be used for the treatment of acute or chronic bacteria-associated enteric disorders in a mammal, in particular gastroenteritis, ulcerative colitis, diarrhoeal diseases.

In another embodiment of the invention, there is provided a antibacterial and/or virucide composition comprising a compound of the invention.

In a further aspect the present invention, there is provided a method of preventing and/or treating acute or chronic pathogen-associated, e.g. bacteria-associated, enteric disorders in a mammal; in particular gastroenteritis or ulcerative colitis, the method comprising administering to said mammal a therapeutically effective amount of a compound of the invention.

In yet a further aspect the present invention, there is provided a method of preventing, reducing and/or inhibiting the invasion and infection of mammalian cells, e.g. mammalian gut cells, mammalian epithelial intestinal cells, by pathogen, in a mammal comprising administering to said mammal a therapeutically effective amount of a compound of the invention.

In yet a further aspect the present invention provides a screening method, e.g. adhesion assay, to test the anti-adhesive activity of a saccharide, e.g. an oligosaccharide, which method comprises a) adding saccharide, e.g. oligosaccharide, solution to cell monolayers of the human colonic cell line HT29 grown to 90%+, e.g. 95 to 100% confluence, in triplicate wells, e.g. 12-well tissue culture plates, b) adding bacterial culture, e.g. grown in tissue culture medium anaerobically at 37° C., e.g. exponential phase culture, e.g. diluted in phosphate buffered saline, e.g. an equal volume thereof, c) washing of the cell layers after 2 h at 37° C. aerobic, 5% $CO_2$, e.g. with phosphate buffered saline (PBS), e.g. several times, e.g. three times, d) detaching cell layers e.g. with trypsin/EDTA solution, e) enumerating bacteria e.g. by plate counting, and f) comparing counts in wells with saccharides, e.g. oligosaccharides, to those without.

According to the invention the screening method may further comprise g) performing dose response curves for saccharides, e.g. oligosaccharides, showing antiadhesive activity, and/or h) determining the effect of the saccharide, e.g. oligosaccharide, on other strains of the pathogen, and/or i) determining the effect on beneficial bacteria, e.g. probiotic.

In another embodiment of the invention, the steps a) and b) are as follows:

a) adding saccharide, e.g. oligosaccharide, to the bacterial culture, e.g. grown in tissue culture medium anaerobically at 37° C., e.g. exponential phase culture, e.g. diluted in phosphate buffered saline, b) adding bacterial culture containing the saccharide, e.g. an equal volume thereof, to cell monolayers of the human colonic cell line HT29 grown to 90%+, e.g. 95 to 100% confluence, in triplicate wells, e.g. 12-well tissue culture plates.

In a further aspect of the invention the bacteria culture preparation may include the preparation of subcultures on 3 successive days.

The screening method of the invention is reliable and reproducible and allows a high number of bacteria adhered to the cell monolayer.

Manno-oligosaccharides may be commercially available under the trade name BioMos from Alltech, UK. Chito-oligosaccharide may be commercially available from Primex Ingredients ASA, Norway or France Chitine. Sialyl-oligosaccharide may be commercially available from Sunsial E, Taiyo Kagaku Co; LTD, Japan. Fructo-oligosaccharide may be commercially available under the trade name Raftilose or Actilite: Galacto-oligosaccharides may be commercially available under the trade name Vivinal GOS, Elixor GOS or Oligomate from Borculo Domo Ingredients, The Netherlands. Partially hydrolysed guar gum may be commercially available under the trade name Benefiber® from Novartis Nutrition Corporation. Isomalto-oligosaccharide may be commercially available under the trade name. Isomalto 900 from Showa Sangyo Co, or IMO P900 from Hayashibara, Japan. Oligogalacturonide may be commercially available under the trade name Galursan. Xylo-oligosaccharide may be commercially available from Suntory, Japan, or under the trade name Xylo-oligo 20P or 35P or 95P from Cuntory Limited. Curdlan (beta-1,3-glucan) may be commercially available from WAKO-Pure-Chemical-Industries-LTD, Japan. Caseino-glycomacropeptide may be commercially available from Arla Foods, Denmark. Pectic oligosaccharide may be commercially from Oranges, US. Gentio-oligosaccharide may be commercially available.

The chito oligosaccharide according to the invention is made by hydrolysis of chitin. It may be a breakdown product of the precursor polysaccharide. Preferably, the chito oligosaccharide according to the invention is produced by Primex Ingredients ASA, Norway or France Chitine.

The sialyl oligosaccharide according to the invention is a complex oligosaccharide, e.g. a mixture of oligosaccharides, e.g. of different size and structure, which may be terminated by sialic acid residues. The sialyl oligosaccharide according to the invention may be a mixture of proteins and oligosaccharides, e.g. a mixture of proteins and sialyl oligosaccharides. The sialyl oligosaccharide according to the invention may be isolated from egg yolk. Preferably, the sialyl oligosaccharide according to the invention may be produced by Sunsial E, Taiyo Kagaku Co; LTD, Japan.

Preferably, the sialyl oligosaccharide according to the invention does not comprise the saccharides known as sialyl Lewis$^x$ (sialyl Le$^x$ or SLe$^x$) and/or sialyl Lewis$^4$ (SLe$^4$), and/or an analogue thereof. Preferably, the sialyl oligosaccharide according to the invention does not comprise fucosyl residues.

According to the invention, CGMP refers to the complex sialylated oligosaccharides carried on caseinoglycomacropeptide. CGMP may be released during cheesemaking.

Alpha 1-6 mannobiose, alpha 1-2 mannobiose and alpha 1-3 mannobiose may be obtained enzymatically from mannose.

To obtain alpha 1-6 mannobiose, the fungal strain *Aspergillus phoenicis*, e.g. *A. phoenicis* ATCC 14332, may be grown in mineral medium, e.g. at pH 5, with BioMOS (Alltech, UK) as sole carbon source, e.g. with 1% BioMOS, under agitation, e.g. on orbital shaker. The incubation condition may be e.g. 30° C., during several days, e.g. 3 days. The inoculation may be done at 10E5 spores/ml. Yield may be about 25%. Enzyme products may then be concentrated, e.g. by ultrafiltration, e.g. 10000 MW cut off, of a sterile filtrate of the incubation medium. The alpha 1-6 mannobiose may then be separated from the monosaccharides e.g. using a P2 gel filtration column, as known to one skilled in the art.

In order to prepare 1,3-alpha-mannosidase, *A. phoenicis* may be incubated during a longer time with BioMOS, e.g. seven days, which results in a production of a second enzyme able to synthetize both alpha-1,6- and alpha-1,3-mannooligosaccharides. Alpha-1,3-mannooligosaccharides may then be purified by technique readily known to one skilled in the art.

In order to prepare alpha 1-2 mannobiose, *Aspergillus oryzae*, e.g. PM-1, recombinant, overproducer of *Penicillium citrinum* alpha 1-2 mannosidase may be incubated in DPY medium, e.g. at pH comprised between 3.5 and 6.0, and comprising mannose, e.g. 70% by weight mannose, based on the total weight of the incubation solution. The incubation condition may be e.g. 55° C., during several days, e.g. 8 days. DPY medium is described in Yoshida et al, 1998, Biosci. Biotechnol. Biochem 62, 309-315, the content of which being hereby incorporated by reference.

The pectic oligosaccharide according to the invention is made by hydrolysis of chitin. It may be a breakdown product of the precursor polysaccharide. The pectic oligosaccharide according to the invention contains a backbone of alpha 1-4 linked galacturonic acid residues with varying chain length. It may be a complex oligosaccharides, e.g. a mixture of oligosaccharides with varying chain lengths. Some of the oligosaccharides contained in the pectic oligosaccharide according to the invention might contain rhamnose- and galactose-containing oligosaccharide chains.

The pectic oligosaccharides may be obtained through the process described in Olano-Martin E, Mountzouris K C, Gibson G R & Rastall R A (2001), "Continuous production of pectic oligosaccharides in an enzyme membrane reactor", Journal of Food Science 66, 966-971, the content of which being hereby incorporated by reference.

It will be appreciated that such process is readily known to one skilled in the art.

As used herein the term probiotic refers to microorganisms, e.g. live microorganisms, which beneficially affect the host by improving its intestinal microbial balance, such as lactobacilli and bifidobactria.

As used herein, the term pathogen refers to non beneficial bacteria, viruses, fungi, monocellular or multicellular parasites, toxins and heavy metal cations, for example *E. coli*, e.g. verocytotoxic *E. coli* (VTEC), enteropathogenic *E. coli* (EPEC), enterotoxigenic *E. coli* (ETEC) or enteroaggregative *E. coli* (EAggEC), *Staphylococcus aureus*, e.g. methicillin-resistant *Staphylococcus aureus* (MRSA), *Clostridium difficile* or toxins of *Clostridium difficile*, Sulphate Reducing bacteria, e.g. *Desulfovibrio* spp, e.g. *Desulfovibrio desulfuricans* or *Desulfovibrio piger*.

The screening method of the invention will now be described in more detail. A culture of the human colonic cells line HT29 is prepared and put into wells, e.g. 12 or 24-well tissue culture plates. The cells may grow to 90% or more confluence, preferably 90 to 100%, more preferably 95 to 100%. The cells may be washed, e.g. with Phosphate Buffer Saline (PBS) buffer, at least once. A bacterial culture is prepared, e.g. in Dulbecco's modified eagle medium (DMEM), or in anaerobic tissue culture medium, e.g. Postgate's Medium E, e.g. at 37° C. The bacterial culture may be prepared e.g. by inoculation from agar cultures the day prior to the experiment or inoculation from broth cultures that had been subcultured daily for seven days. The bacterial culture may be grown until stationary or logarithmic phase, preferably until exponential phase. The bacterial culture may be diluted 1/500 to 1/10000, more preferably 1/1000, in cell culture medium, e.g. DMEM, or PBS, preferably in PBS, before being added to the cells. The bacterial, e.g. diluted bacterial, culture may be added to the cells in equal volume. The tested oligosaccharide may be added to the bacterial culture, preferably before incubating the culture with the cells. Alternatively, the tested oligosaccharide may be added to the HT29 monolayers and immediately followed by bacterial suspension. The tested oligosaccharide may be used in a concentration comprised between about 0.05 and 100 mg/ml, preferably between about 0.1 and 50 mg/ml, preferably between about 0.25 and 15 mg/ml, preferably between about 0.5 and 10 mg/ml, more preferably between about 2 and 5 mg/ml, even more preferably at about 2.5 mg/ml. Before to be added to the bacterial culture, the oligosaccharides may be subject to purification, e.g. deproteination, e.g. with proteases. Such purification methods are well known in the art. The bacterial culture may be incubated with the cells for several hours, preferably from about 1 to about 5 hours, more preferably about 2 hours. The incubation may be done at a temperature comprised between about 35 and about 40° C., preferably at about 37° C. The incubation may be aerobic, e.g. 5% $CO_2$. The bacteria which don't adhere to the cells may be removed by washing the cells layers, e.g. with PBS, e.g. several times, e.g. three times. The cells may then be removed from the culture plate e.g. by an enzyme/chelator solution, e.g. a trypsin/EDTA solution, e.g. during from about 30 seconds to about 2 minutes. After resuspension, the cells may be mixed to break up clumps. The adhered bacteria may then be enumerated and compared to the oligosaccharide-free control. Counting of the bacteria may be done by using an enzyme-based assay, such as beta-galactosidase activity, or a limulus amoebocyte lysate assay. It will be appreciated that such assays are readily known to one skilled in the art, and are available as commercial kits. According to the invention, prior to applying to the HT29 monolayer the bacteria may be stained, e.g. fluorescently labeled, and the adhered bacteria may be counted with a flow cytometer. Preferably, the adhered bacteria are counted by direct counting e.g. after plating onto plate count agar.

In one aspect of the invention, there is provided a medicament, nutritional or pharmaceutical formulation, for example dietary supplement, comprising a compound of the invention. For the purpose of the invention, the term "composition of the invention" encompasses compositions comprising at least one compound of the invention.

The compositions of the invention may further comprise one or more of the following: proanthocyanidins, lactoferrin, linoleic acid and linolenic acid.

The medicament, nutritional or pharmaceutical composition of the invention may optionally comprise pharmaceutical acceptable carriers. Further, according to the invention there is provided a combined pharmaceutical preparation for simultaneous, separate or sequential use for inhibiting pathogen adhesion to mammalian cells, e.g. for controlling, e.g. treating, preventing or ameliorating acute or chronic bacteria-associated enteric disorders in a mammal.

The compositions of the invention optionally comprise conventional food additives, such as any of emulsifiers, stabilizers, sweeteners, flavourings, colouring agents, preservatives, chelating agents, osmotic agents, buffers or agents for pH adjustment, acidulants, thickeners, texturisers, and so on.

Pharmaceutical compositions and dietary supplements may be provided in the form of soft gel, sachets, powders, syrups, liquid suspensions, emulsions and solutions in convenient dosage forms. In soft capsules the active ingredients are preferably dissolved or suspended in suitable liquids, such as fatty oils, paraffin oil or liquid polyethylene glycols. Optionally stabilisers may be added.

The amount of compound of the invention incorporated into the compositions of the invention may depend on the nature and/or the molecular weight of the saccharide, the form of the compositions of the invention, e.g. a powder or a composition ready-for-consumption. Accordingly, suitable amounts of compound of the invention comprised in compositions according to the invention are in the range of up to about 80% by weight, e.g. up to about 60% by weight, or up to about 40% by weight, for example from about 0.05 to about 50% by weight, e.g. from about 0.5 to about 20% by weight, e.g. about 2.5 to about 10%, e.g. about 1% by weight, based on the total weight of the composition.

The amount and dosage regimen of the compositions of the invention to be administered is determined in the light of various relevant factors including the purpose and manner of administration, the age, sex, body weight and overall health and condition of individual subject and the severity of the subject's symptoms. When the composition according to the invention is supplied in the form of a food or beverage, a suitable serving size of the compound of the invention may be from about 1 mg to about 20 g, preferably from about 10 mg to about 10 g, more preferably from about 10 mg to about 1 g. If provided in pharmaceutical form, suitable daily doses of the compound of the invention are up to about 250 mg, preferably up to about 150 mg, more preferably up to about 100 mg, and optimally in the range of about 1 mg to about 100 mg. In terms of body weight, daily dosage may vary between from about 0.05 mg to about 5 g/kg body weight/day, preferably from about 0.5 mg to about 3 g/kg body weight/day, more preferably more than 1 mg/kg body weight/day, and even more preferably about 1 mg/kg body weight/day. The daily dosage may correspond to a single unit dosage, or may be provided through multiple unit dosages. The exact amounts of the compound according to the invention may vary between wide limits and may be readily determined in conventional manner.

The amount and dosage regimen of the compound of the invention to be administered is determined in the light of various relevant factors including the purpose and manner of administration, the age, sex, body weight and overall health and condition of individual subject and the severity of the subject's symptoms. A suitable range may be between about 50 µg and 10 g/day, preferably between about 0.5 mg and 5 g/day, more preferably between about 5 mg and 3 g/day e.g. for a 70 kg patient.

According to the invention, a "therapeutically effective amount" refers to an amount efficient to prevent, reduce r inhibit the adhesion of pathogen, in particular pathogenic gut bacteria, to mammalian cells, e.g. mammalian gut cells or mammalian epithelial intestinal cells, i.e. to prevent or treat acute or chronic pathogen-associated, e.g. bacteria-associated, enteric disorders.

Pharmaceutical or dietary supplement forms may be made by conventional compounding procedures known in the pharmaceutical art, that is, by mixing the active substances together with edible pharmaceutically acceptable solid or liquid carriers and/or excipients, e.g. fillers such as cellulose, lactose, sucrose, mannitol, sorbitol, and calcium phosphates and binders, such as starch, gelatin, tragacanth, methylcellulose and/or polyvinylpyrrolidone (PVP). Optional additives include lubricants and flow conditioners, e.g. silicic acid, silicon dioxide, talc, stearic acid, magnesium/calcium stearates, polyethylene glycol (PEG) diluents, disintegrating agents, e.g. starch, carboxymethyl starch, cross-linked PVP, agar, alginic acid and alginates, colouring agents, flavouring agents, and melting agents. Dyes or pigments may be added to the tablets or dragée coatings, for example for identification purposes or to indicate different doses of active ingredient.

Optionally, the compositions according to the invention may be nutritionally complete, i.e. may include vitamins, minerals, trace elements as well as nitrogen, carbohydrate and fatty acid sources so that they may be used as the sole source of nutrition supplying essentially all the required daily amounts of vitamins, minerals, carbohydrates, fatty acids, proteins and the like. Accordingly, the compositions of the invention may be provided in the form of a nutritionally balanced complete meal, e.g. suited for oral or tube feeding.

Alternatively, the compositions of the invention may be provided as part of a meal, i.e. a nutritional supplement, e.g. in the form of a health drink.

It may be desirable to provide the composition of the invention in the form of a low calorie meal replacement or other nutritional product. In this case the meal replacement or other nutritional product is preferably low fat, i.e. less than about 10 en %, or substantially fat-free, i.e. less than about 2.5 en % contributed by fat, such as about 2 en % fat, based on the total caloric content of the composition. Suitably, a single serving of a low calorie meal replacement will have a caloric value of less than about 1000 kcal, and preferably between about 200 kcal and about 500 kcal.

Suitable compositions of the invention, e.g. suitable low calorie nutritional product, may include soft drink, such as juice, smoothie or soy-based drink, or dispersed in foods of any sort, such as, dairy bars, soups, breakfast cereals, müesli, candies, tabs, cookies, biscuits, spreads, infant formula, weaning food, confectionery, cakes, crackers, such as a rice crackers, and dairy products, such as milk-shake, yoghurt drink, fermented milk.

The compositions of the invention optionally comprise conventional food additives, such as any of emulsifiers, stabilizers, sweeteners, flavourings, colouring agents, preservatives, chelating agents, osmotic agents, buffers or agents for pH adjustment, acidulants, thickeners, texturisers, and so on.

In a further aspect of the invention, there is provided a use of compound or compositions of the invention as food additive.

Suitable product formats according to the present invention include solution, ready-for-consumption composition, e.g. ready-to-drink compositions, instant drink, liquid comestibles, like soft drinks, juice, sports drinks, milk drinks, milk-shakes, yogurt drinks or soup. In a further embodiment of the invention, the compositions of the present invention may be manufactured and sold in the form of a concentrate, a powder, or granules, e.g. effervescent granules, which are diluted with water or other liquid, such as milk or fruit juice, to yield a ready-for-consumption composition, e.g. ready-to-drink compositions or instant drink.

The composition of the invention may be in any form suitable for human administration, and in particular for admiration in any part of the gastrointestinal tract. Enteral administration of the compositions of the invention, and preferably oral administration, and administration through a tube or catheter, are covered by the present invention.

The compositions of the invention may be administered under the supervision of a medical specialist, or may be self-administered.

Pharmaceutical, food or beverage incorporating compound according to the invention can be safely-consumed by anyone, and are especially recommended for anyone perceived to be at risk from diseases, conditions and symptoms related to Inflammatory bowel disease (IBD), in particular Ulcerative Colitis and Crohn's disease, colon cancer, Inflammatory bowel disease (IBS), acute or chronic bacteria-associated enteric disorders, e.g. infection of the gastrointestinal tract.

In one embodiment of the invention, the invention pertains to a method of treating and/or preventing e.g. acute or chronic bacteria-associated enteric disorders, IBD, IBS and/or damages of the cells of the gastrointestinal tract caused by toxins or heavy-metal cations, in a mammal, including human, in need of such a treatment, comprising administering to said mammal an effective amount of a compound or composition according to the invention. As used herein, the term "an effective amount" refers to an amount effective to achieve a desired therapeutic effect, such as treating and/or preventing acute or chronic bacteria-associated enteric disorders and/or infection of the gastrointestinal tract.

In another embodiment of the invention, there is provided a method for inhibiting pathogen adhesion to mammalian cells, e.g. to gut or intestinal epithelial mammalian cells.

In a further embodiment, the present invention relates to a process for the production of the compositions of the invention, wherein such process comprises intimately admixing the components of the composition of the invention with pharmaceutically or nutritionally acceptable excipients. Such processes are well known to one skilled in the art.

The utility of all the compositions of the present invention may be observed in standard clinical tests in, for example, indications as described hereinabove, for example using nutritional compositions as described in the Examples hereinbelow, for example using one or more compound of the invention, in a range of from about 1 g to 15 g, e.g. about 10 g, for a mammal, e.g. adult and in standard animal models. The relief in symptoms characterizing acute or chronic bacteria-associated enteric disorders provided by the compositions may be observed in standard animal tests and in clinical trials, e.g. as monitored by any of the methods known to one skilled in the art, e.g. by analyzing the feacal microflora, e.g. Desulfobrio, or Sulphate reducing bacteria.

One human clinical trial may be affected as follows:

A randomized blind, placebo controlled, parallel study in e.g. 100 subjects may be performed using the composition of the invention. The subjects may receive several times, e.g. three times, a composition of the invention comprising FOS, e.g. in a range of about 6 g/day. Faecal samples may be collected at baseline, after 14 days of treatment and after 28 days of treatment, and faecal bacteria, e.g. Clostridia, may be counted by Fluorescent in situ Hybridisation (FISH), e.g. employing oligonucleotide probes targeting 16S rRNA.

Figure 1:
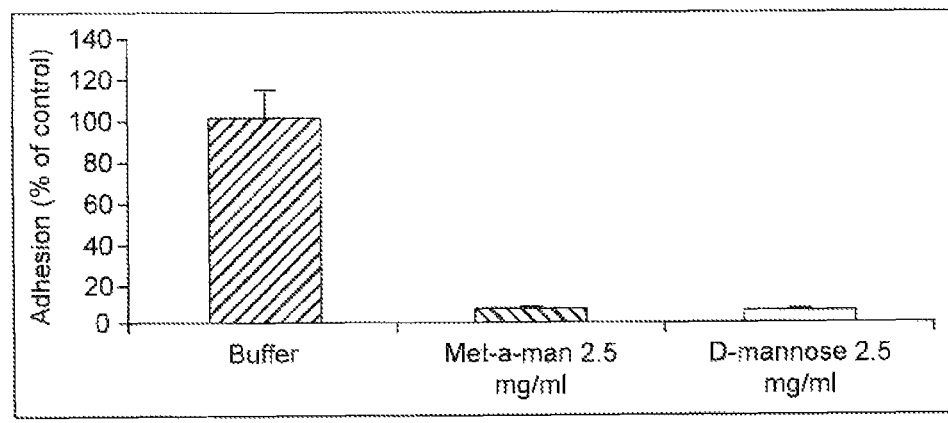
FIG. 1. Inhibition of adhesion of VTEC to HT29 cells by methyl-~-D-mannopyranoside and D-mannose, indicating that adhesion is mediated by type I fimbriae. Error bars indicate standard error. Numbers of adhered bacteria are expressed as a percentage of the numbers adhered in the oligosaccharide-free control in each experiment.

The invention is now further illustrated by the following examples:

EXAMPLES

Microbiological media are from Oxoid Ltd., Basingstoke, UK: plate count agar (PCA); de Mann Rogosa Sharpe agar and broth (MRSA and MRSB); maximum recovery diluent (MRD); yeast extract; agar no. 1 in the Postgate's media, maximum recovery diluent (MRD). All are prepared according to the manufacturer's instructions, except for the latter where 0.1 g/l of ascorbic acid and sodium thioglycollate are added and transferred to the anaerobic cabinet immediately after removal from the autoclave.

The following chemicals are from Sigma-Aldrich Chemical Co. Ltd., Poole, UK: Phosphate buffered saline tablets (PBS; pH 7.2±0.2, cat. no. P4417); MEM non-essential amino acid solution (cat. no. M7145); Trypsin-EDTA solution (T4299, 500 BAEE units porcine trypsin and 180 μg EDTA per ml); Postgate's media.

The following are from GIBCO, Invitrogen Ltd., Paisley, UK: Dulbecco's, Modified Eagle Medium with Glutamax-1 (DMEM; cat no. 61965-02); Foetal bovine serum (FBS; cat. no. 10106-169).

HT29 human colon adenocarcinoma epithelial cells are obtained from the European Collection of Cell Cultures (ECACC), Centre for Applied Microbiology and Research, Porton Down, UK (cat. no. 91072201). Cells are grown in 25 cm$^2$ tissue culture flasks in SDMEM at 37° C. in 5% $CO_2$ until ca. 90% confluent, split according to ECACC recommended method, and stored in aliquots over liquid nitrogen. These aliquots are used to seed 25 cm$^2$ flasks, which after growth were split into 12-well tissue culture plates. The 12-well plates are grown to Ca. 90% confluence before being used in the adhesion assays.

Non-toxigenic *Escherichia coli* O157:H7 isolates are obtained from the National Collection of Type Cultures, Colindale, London, UK.

Enteropathogenic *E. coli* (EPEC) isolates are resuscitated from freeze-dried ampoules stored at ambient temperature since 1976. These are originally obtained from the *Salmonella* and *Shigelia* Reference Laboratory, Public Health Laboratory Service (now Health Protection Agency), Colindale, London, UK, and are isolated from infant diarrhoea cases. The strains used are listed in Table 1.

| Pathovar | Serotype | Strain number |
| --- | --- | --- |
| Verocytotoxic (Stx) (VTEC) | O157:H7 | NCTC 12900 |
| | O157:H7 | NCTC 13128 |
| | O157:H7 | NCTC 13129 |
| Enteropathogenic (EPEC) | O111:H27 | E.4946/76 |
| | O119:H4 | E.4821/76 |
| | O128:H12 | E4824/76 |

Bacterial isolates are stored at −80° C. on cryogenic culture storage beads. Working cultures on slopes of PCA in universal bottles are prepared from the beads and stored for up to one month at 4° C. A PCA plate is streaked each time the slope cultures are used in order to check culture purity.

*Desulfovibrio desulfuricans* NCIMB 12833 is obtained from the National Collection of Industrial and Marine Bacteria, UK. The strain is cultured in PEM in Hungate tubes, anaerobicaily at 37° C. for up to five days. Working cultures in Hungate tubes are stored for up to two months at ambient temperature. To prepare cultures for the adhesion assay, 1.0 ml of stock culture is inoculated into a Hungate tube and incubated for 24 h. A 1 ml aliquot is taken from this tube, inoculated into a fresh Hungate tube and incubated for a further 24 h.

The carbohydrates used are listed in Table 2:

| Short name | Full name/chemical structure | Origin |
| --- | --- | --- |
| Benefiber | Partially hydrolysed guar gum | Novartis Consumer Health |
| BioMOS | Manno-oligosaccharides | Alltech, UK |
| CGMP | Casein glycomacropeptide | Arla Foods, Denmark |
| ChOS | Chitosan oligosaccharide, 97% deacetylated. | Shrimp shells. Primex Ingredients ASA, Norway |
| Curdlan | β-1,3-glucan | Wako Pure Chemical Industries Ltd., Japan |
| Dextran 11.6 kDa | Dextran 11.6 kDa | Sigma-Aldrich, UK |
| Dextran 42 kDa | Dextran 42 kDa | Sigma-Aldrich, UK |
| IMO P900 | Isomalto-oligosaccharide | Hayashibara, Japan |
| Lactose | Lactose | Sigma-Aldrich, UK |
| Lactulose | | Sigma-Aldrich, UK |
| Maltodextrin G20 | | ABF, UK |
| Maltodextrin G30 | | ABF, UK |
| Maltotriose | α-1,4-linked glucopyranose units | Sigma-Aldrich, UK |
| Meth mann | Methyl-α-D-mannopyranoside | Sigma-Aldrich, UK |
| POS | Pectic oligosaccharide | From oranges; gift from USDA |
| Pectin | Pectin | From oranges; gift from USDA |
| SiOS | Sialyloligosaccharide | Sunsial, Taiyo Kagaku Co. Ltd., Japan. |
| vGOS | Galacto-oligosaccharide | Borculo Domo Ingredients, The Netherlands. |
| vGOS-mono | vGOS with monosaccharides removed by ultrafiltration | Borculo Domo Ingredients, The Netherlands, purified in-house |

-continued

| Short name | Full name/chemical structure | Origin |
|---|---|---|
| XOS | Xylo-oligosaccharide | Suntory, Japan |
| HM pectin | High methoxy pectin (63-66%) | Citrus peel; Fluka Biochemika |
| LM pectin | Low methoxy pectin (6%) | Apple; BDH Ltd. |

Inhibition of *E. coli* Adhesion

Example 1

HT29 cells were grown to 95-100% confluence in 12-well tissue culture plates. Bacterial cultures were grown in tissue culture medium, anaerobically at 37° C. These incubation conditions promoted expression of adhesions by the bacteria. The bacteria (in buffer, with or without the test oligosaccharide) were added to the cell monolayers and incubated for 2 h at 37° C. aerobically under 5% $CO_2$. After incubation, the cell layers were washed three times in buffer and the adherent bacteria quantified. Assays were performed in triplicate The tested oligosaccharides were methyl-α-mannopyrannoside and CGMP.

After the adhesion and washing stages, the cells were suspended and vigorously mixed to break up clumps. The resulting suspension was then plated onto non-selective agar media appropriate for the test organism.

The Initial inoculum was 7.3 log cfu $ml^{-1}$ (VTEC) and 7.0 log cfu $ml^{-1}$ (EPEC).

| Bathing medium (oligosaccharide concentrations were 0.25%) | Viable count of adhered VTEC (log cfu $ml^{-1}$) | Viable count of adhered EPEC (log cfu $ml^{-1}$) |
|---|---|---|
| buffer only | 6.3 | 5.3 |
| methyl-α-mannopyranoside | 4.8 | 5.1 |
| casein glycomacropeptide | 5.8 | 4.8 |

A reduction in adhesion was achieved with methyl-α-mannopyranoside. Casein glycomacropeptide slightly reduced the adhesion of enteropathogenic *E. coli*.

Example 2

VTEC NCTC 12900 was inoculated from frozen stocks into Dulbecco's modified eagle medium (DMEM) with added non-essential amino acids (1% v/v) and foetal bovine serum (5% v/v). The culture was incubated anaerobically at 37° C. for 18 h. A 20 μl aliquot was transferred into 2 ml of fresh DMEM, and incubated under the same conditions for 24 h. This was repeated twice more, so that the organism was subcultured on three successive days. An adhesion assay was then carried out as described previously, using 2.5 mg ml methyl-α-D-mannopyrannoside and D-mannose, and the adhered bacteria were enumerated by using plate counting.

The results indicated good inhibition of adhesion with both methyl-α-D-mannopyrannoside and D-mannose (FIG. 1).

Alpha 1,2 mannobiose and alpha 1,6 mannobiose were assayed for anti-adhesive activity using the method described hereinabove, with the modification that the VTEC cultures were subcultured on three successive days as described above. Inhibition of adhesion was detected for both mannobiose sugars and the control (FIG. 2).

Further oligosaccharides (pectic oligosaccharides, isomalto-oligosaccharides, GOS, partially hydrolyzed guar gum, xylo oligosaccharides and lactulose) have been tested for anti-adhesive activity against *E. coli*, both VTEC and EPEC pathovars. Methods were as described previously but with three subcultures included in the culture preparation stage, as described above. Compounds tested included GOS and pectic oligosaccharides that had been further purified by ultrafiltration to remove nitrates.

FIG. 1. Inhibition of adhesion of VTEC to HT29 cells by methyl-α-D-mannopyranoside and D-mannose, indicating that adhesion is mediated by type I fimbriae. Error bars indicate standard error. Numbers of adhered bacteria are expressed as a percentage of the numbers adhered in the oligosaccharide-free control in each experiment.

Figure 2:
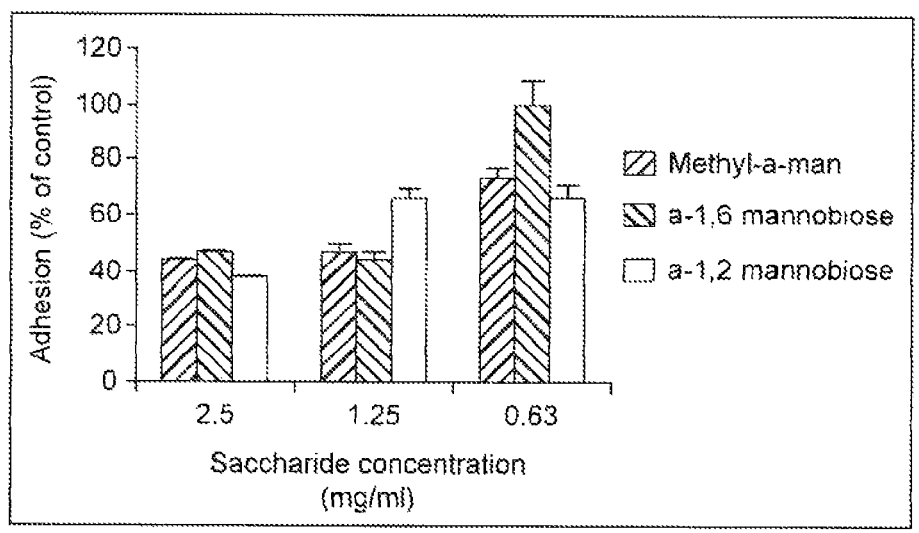
FIG. 2. Inhibition of adhesion of VTEC to HT29 cells by methyl-alpha-d-mannopyranoside, alpha-1,6- and alpha-1,2-mannobiose. Error bars indicate standard error.

FIG. 2. Inhibition of adhesion of VTEC to HT29 cells by methyl-alpha-d-mannopyranoside, alpha-1,6- and alpha-1,2-mannobiose. Error bars indicate standard error.

Figure 3:
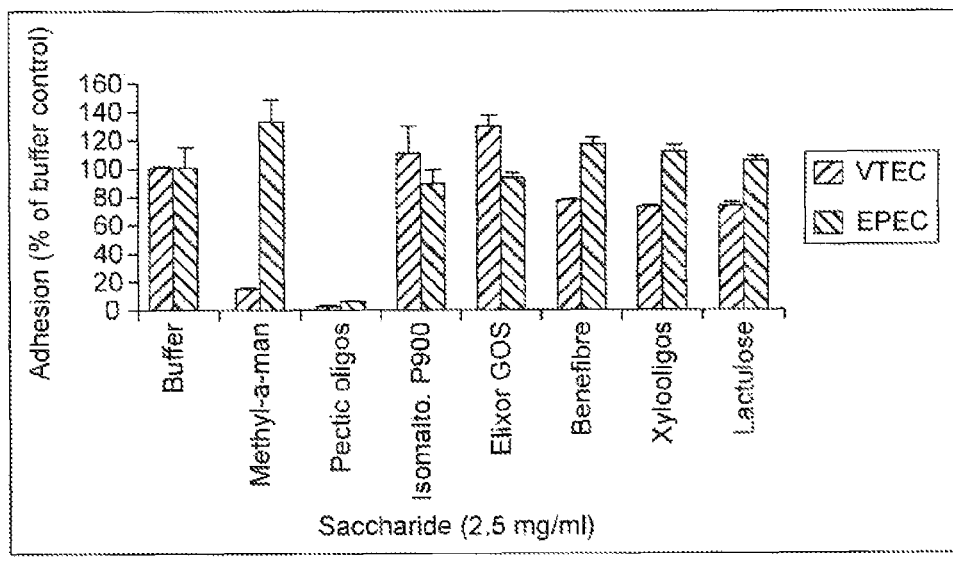
FIG. 3. Anti-adhesive activity of selected saccharides against VTEC and EPEC. The pectic oligosaccharides show powerful anti-adhesive activity against both VTEC and EPEC (FIG. 3).

FIG. 3. Anti-adhesive activity of selected saccharides against VTEC and EPEC. The pectic oligosaccharides show powerful anti-adhesive activity against both VTEC and EPEC (FIG. 3).

Example 3

The saccharides were tested against one strain of *E. coli* VTEC (0157:1H7 strain NCTC 12900) and one strain of *E. coli* EPEC (O119:H4).

Method

*E. coli* broth cultures for adhesion assays were grown in DMEM supplemented with 5% v/v FBS and 1% non-essential amino acid solution (SDMEM). For each strain, a broth was inoculated from a slope culture and incubated anaerobically at 37° C. for 18-24 h. The overnight culture was then inoculated (1% v/v) into fresh SDMEM and incubated for a further 18-24 h under the same conditions. This was repeated once more. On the day of the assay, a 10% v/v inoculum was placed into pre-warmed SDMEM and incubated for 4 h anaerobically at 37° C.

A culture of the test strain was prepared as described above, then diluted 1:500 in PBS. The viable count of the diluted suspension was determined by spread plating onto PCA, with decimal dilutions carried out in MRD as necessary. The carbohydrates to be tested were dissolved in PBS (5 mg/ml) and sterilised by passing through a 0.2 μm syringe filter. The carbohydrate solutions were further diluted in sterile PBS if required. The SDMEM was aspirated from a 12-well tissue culture plate with near-confluent monolayers of HT29 cells (described above). The monolayers were washed by pipetting in 1 ml sterile PBS per well, swirling by hand, and then aspirating. A 0.5 ml aliquot of carbohydrate solution was added to a well, followed by 0.5 ml of the bacterial suspension in PBS. A control using sterile PBS in place of carbohydrate solution was prepared. All assays were performed in triplicate. The plates were swirled by hand to mix, then incubated at 37° C. aerobically for 2 hours. After incubation, the bacterial suspension was aspirated from the wells. A 1 ml aliquot of PBS was added to each well, the plate was swirled briefly by hand, and the PBS was removed. This washing step was repeated twice more. A 70 µl aliquot of trypin-EDTA solution was added to each well, the plate was rocked to ensure even coverage, and then incubated at 37° C. for 5 min. A 1 ml aliquot of PBS was then pipetted into each well, and pipette mixed until the monolayer was completely dislodged and clumps broken up (as determined visually). The bacteria remaining in the well were then enumerated by plate counting on to PCA, with decimal dilutions performed in MRD as required. All plates were incubated at 37° C. for 18-24 hours before colonies were enumerated.

Data processing: Viable counts were calculated for all wells and the inoculum, and expressed as colony forming units per ml (cfu/ml). For each test, the mean and standard error of the triplicate wells were calculated. For each well, the number of adherent bacteria was calculated as a percentage of the mean of the control (carbohydrate-free) wells, and as a percentage of the inoculum (adjusted for dilution by the carbohydrate solution).

Figure 4:
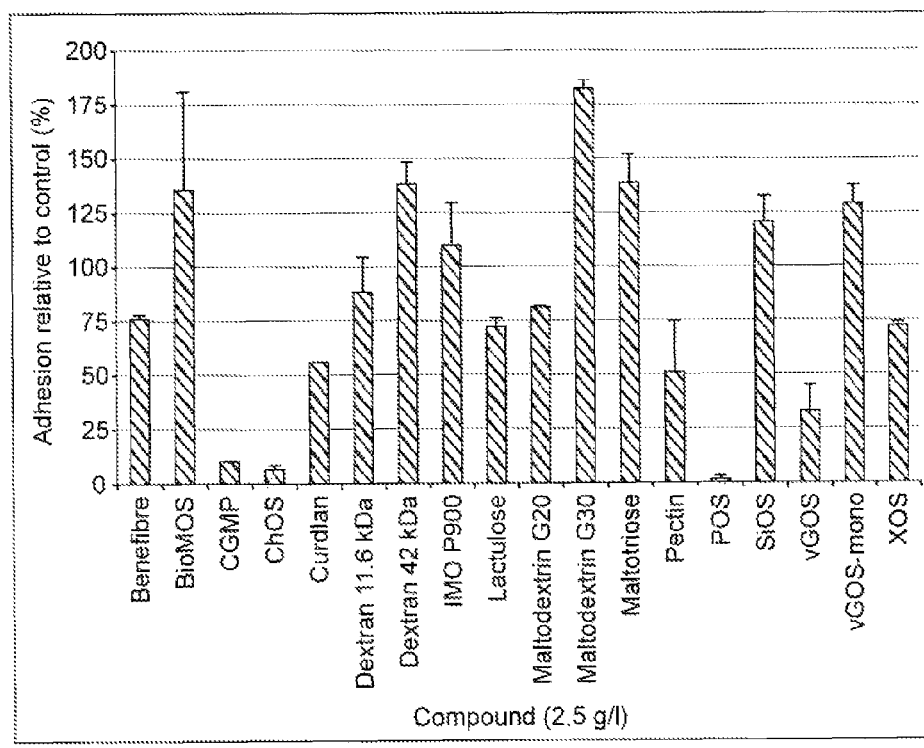
FIG. 4. Anti-adhesive activity of carbohydrate compounds against *E. coli* VTEC (O157:H7 NCTC 12900).

FIG. 4. Anti-adhesive activity of carbohydrate compounds against *E. coli* VTEC (O157:H7 NCTC 12900).

Figure 5:
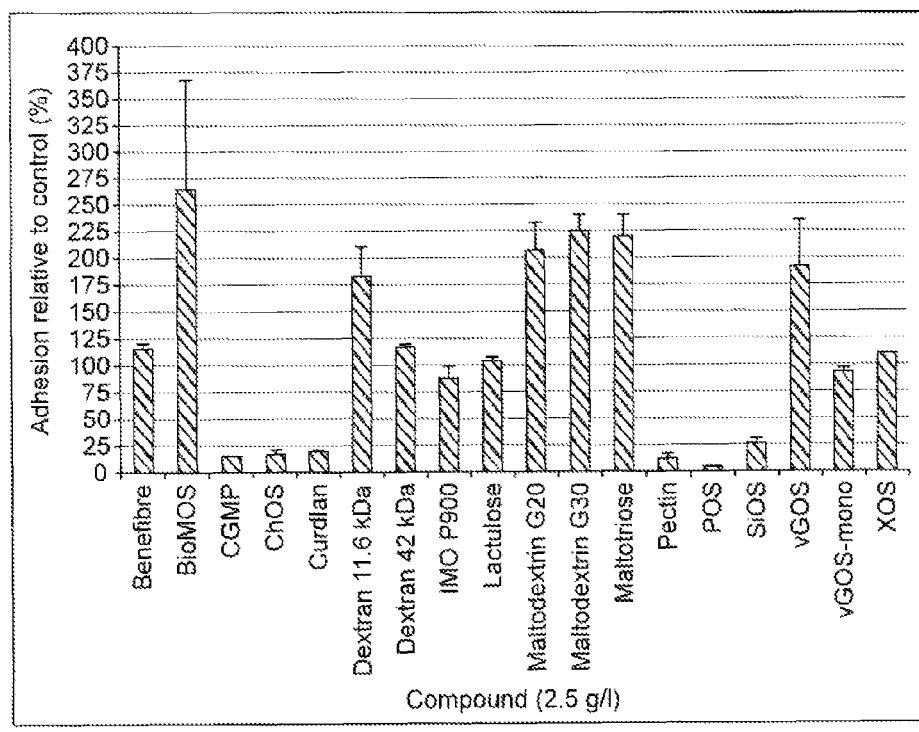
FIG. 5. Anti-adhesive activity of carbohydrate compounds against enteropathogenic *E. coli* EPEC (O119:H49). Error bars indicate standard error of the mean of triplicate assays.

FIG. 5. Anti-adhesive activity of carbohydrate compounds against enteropathogenic *E. coli* EPEC (O119:H49.

Error bars indicate standard error of the mean of triplicate assays.

Results

CGMP, ChOS and POS are positive for both pathovars of *E. coli*, vGOS was positive for *E. coli* VTEC (O157-H7), and curdlan, pectin and SiOS were positive for *E coli* EPEC. Several compounds increased the number of adhered bacteria relative to the carbohydrate-free control. This may be due to the presence of substrates that can be assimilated in the carbohydrate preparation and subsequent growth of the *E. coli* during the 2 hour test incubation period.

Inhibition of Sulphate Reducing Bacteria Adhesion

Example 4

Method

Postgate's E medium (PEM) was prepared by combining the following ingredients in a conical flask: $KH_2PO_4$ 0.5 g, $NH_4Cl$ 1.0 g, $Na_2SO_4$ 1.0 g, $CaCl_2$ 0.51 g, $MgCl_2 \cdot 7H_2O$ 2.0 g, sodium lactate 3.5 g, yeast extract 1.0 g, ascorbic acid 0.1 g, sodium thioglycollate 0.1 g, $FeSO_4 \cdot 7H_2O$ 0.5 g, tap water 1 L. The medium was boiled to dissolve the ingredients and cooled to approximately 50° C. The pH was adjusted to 7.6 with 1.0 M $NaOH_{(aq)}$. The medium was re-boiled and transferred immediately to an anaerobic cabinet (80% $N_2$, 10% $CO_2$, 10% $H_2$, 37° C.), allowed to cool until hand-hot, and dispensed into Hungate tubes (10 ml/tube). The Hungate tubes were autoclaved at 121° C. for 15 minutes. Postgate's E agar (PEA) was prepared as above but with the addition of 15 g agar no. 1. After pH adjustment, the agar medium was dispensed into screw-capped bottles and autoclaved at 121° C. for 15 minutes. the agar was cooled to 50° C. and dispensed into Petri dishes. Once set, the agar plates were transferred into the anaerobic cabinet four days prior to use.

The microbiological media were from Oxoid Ltd., Basingstoke, UK. They were transferred to the anaerobic cabinet immediately after removal from the autoclave. The maximum recovery diluent (MRD) was prepared according to the manufacturer's instructions, except for the addition of 0.1 g/l each of ascorbic acid and sodium thioglycollate.

Figure 6:
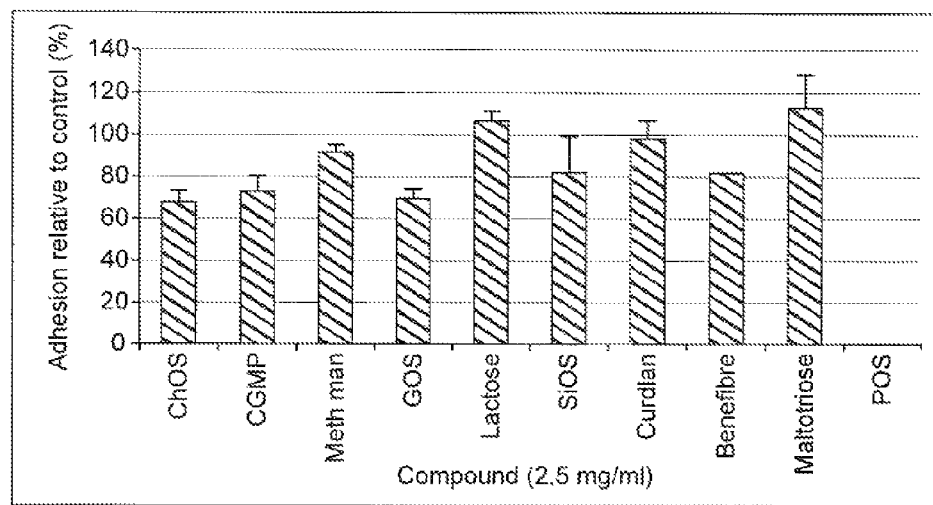
FIG. 6. Anti-adhesive activity of compounds. Error bars indicate the standard error of 5 triplicate assays.

Bacterial adhesion assays were carried out as previously described (Section 3.3.5) except that monolayers were incubated in the presence of bacteria for one hour under anaerobic conditions. Data processing was carried out as described before FIG. 6: Anti-adhesive activity of compounds. Error bars indicate the standard error of triplicate assays. Those marked with an "a" are significantly (P<0.05) lower than the control.

Results

It can be seen that SRB adhesion was inhibited by chito oligosaccharides, galacto-oligosaccharides and pectic oligosaccharides. The pectic oligosaccharides virtually eliminated SRB adhesion to HT29 cells.

Nutritional Composition

Example 5

A nutritional composition in form of biscuit is prepared with the following ingredients:

| | |
|---|---|
| FOS powder[1] | 10 g |
| Wheat flour | 58.9 g |
| Sugar | 8 g |
| Vegetable fat | 16 g |
| Wheat flakes | 6 g |
| Baking powder | 1 g |
| Salt | 0.1 g |

[1]from Borculo Domo Ingredients (The Netherlands).

Example 6

Ready to drink dietary supplement, per 100 ml

| | |
|---|---|
| Pectic-oligosaccharide[2] | 1.25 g |
| Protein | 9 g |
| Carbohydrates | 21.4 |
| Sucrose | 5 g |
| Lactose | 0.7 g |
| Fats | 8.7 g |
| saturated FA | 0.8 g |
| unsaturated FA | 7.4 g |
| Vitamin mix | 7.5 mg |
| Mineral mix | 320 mg |

[2]from Oranges (USA).

The invention claimed is:

1. A nutritional or pharmaceutical composition for the inhibition of pathogenic bacteria adhesion to mammalian cells, or for reducing or inhibiting the invasion and infection of mammalian cells by pathogenic bacteria, wherein the mammal cells invaded or infected are mammalian gut or intestinal epithelial cells, the composition comprising:
   a first compound comprising methyl alpha manno-oligosaccharides in an amount of about 0.5% to about 50% by total weight of the composition; and
   a second compound comprising proanthocyanidins.

2. The nutritional or pharmaceutical composition according to claim 1, wherein the composition further comprises partially hydrolysed guar gum.

3. A nutritional or pharmaceutical composition for the treatment of acute or chronic pathogenic bacteria-associated enteric disorders in a mammal, or for the treatment of pathogenic bacteria microflora proliferation in a mammal, the composition comprising:

a first compound comprising methyl alpha manno-oligosaccharides in an amount of about 0.5% to about 50% by total weight of the composition: and a second compound comprising proanthocyanidins.

4. The nutritional or pharmaceutical composition according to claim 3, wherein said acute or chronic pathogenic bacteria-associated enteric disorders are selected from the group consisting of gastroenteritis, ulcerative colitis, diarrhoeal diseases, and combinations thereof.

5. A method for inhibiting pathogenic bacteria adhesion to mammalian cells or for reducing or inhibiting the invasion and infection of mammalian cells by pathogenic bacteria, the method comprising administering to a mammal a composition comprising: a first compound comprising methyl alpha manno-oligosaccharides, wherein said mammalian cells are those of the gut and intestinal mammalian cells, and wherein the composition comprises about 0.5% to about 50% of the first compound by total weight of the composition; and a second compound comprising proanthocyanidins.

6. A method of treating acute or chronic pathogenic bacteria-associated, enteric disorders in a mammal, said method comprising administering to said mammal a composition comprising: about 0.5% to about 50% of methyl alpha manno-oligosaccharides by total weight of the composition.

7. The method according to claim 6, wherein said enteric disorders are selected from the group consisting of gastroenteritis, ulcerative colitis, diarrhoeal diseases, and combinations thereof.

8. The method according to claim 6, wherein the composition further comprises a therapeutically effect amount of partially hydrolysed guar gum.

9. A nutritional or pharmaceutical composition comprising methyl alpha manno-oligosaccharides, wherein the composition comprises about 2.5% to about 10% of the methyl alpha manno-oligosaccharides by total weight of the composition.

10. A method for the manufacture of a nutritional or pharmaceutical composition for the inhibition of pathogenic bacteria adhesion to mammalian cells, or for reducing or inhibiting the invasion and infection of mammalian cells by pathogenic bacteria, the method comprising adding to the nutritional or pharmaceutical composition a first compound comprising methyl alpha manno-oligosaccharides, wherein the mammalian cells are mammalian gut or intestinal epithelial cells, wherein the composition comprises about 0.5% to about 50% of the first compound by total weight of the composition; and adding to the nutritional or pharmaceutical composition a second compound comprising proanthocyanidin.

11. A method for the manufacture of a nutritional or pharmaceutical composition for the treatment of acute or chronic pathogenic bacteria-associated enteric disorders in a mammal or for the treatment of pathogenic bacteria microflora proliferation in the mammal, the method comprising adding to the nutritional or pharmaceutical composition a first compound comprising methyl alpha manno-oligosaccharides, wherein the composition comprises about 0.5% to about 50% of the first compound by total weight of the composition; and adding to the nutritional or pharmaceutical composition a second compound comprising proanthocyanidins.

12. A method according to claim 11, wherein said enteric disorders are selected from the group consisting of gastroenteritis, ulcerative colitis, diarrhoeal diseases, and combinations thereof.

* * * * *